(12) United States Patent
Krüger et al.

(10) Patent No.: US 10,254,221 B2
(45) Date of Patent: Apr. 9, 2019

(54) METHOD FOR DETERMINING THE UV TRANSMITTANCE OF WATER

(71) Applicant: XYLEM IP MANAGEMENT S.À R.L., Senningerberg (LU)

(72) Inventors: Friedhelm Krüger, Lemgo (DE); Uwe Kanigowski, Velbert (DE)

(73) Assignee: XYLEM IP MANAGEMENT S.À R.L., Luxembourg (LU)

( * ) Notice: Subject to any disclaimer, the term of this patent is extended or adjusted under 35 U.S.C. 154(b) by 0 days.

(21) Appl. No.: 15/543,800

(22) PCT Filed: Jan. 15, 2016

(86) PCT No.: PCT/EP2016/050765
§ 371 (c)(1),
(2) Date: Jul. 14, 2017

(87) PCT Pub. No.: WO2016/113390
PCT Pub. Date: Jul. 21, 2016

(65) Prior Publication Data
US 2018/0011019 A1    Jan. 11, 2018

(30) Foreign Application Priority Data
Jan. 16, 2015    (DE) .................. 10 2015 000 263

(51) Int. Cl.
*G01N 21/59*    (2006.01)
*G01N 33/18*    (2006.01)
(Continued)

(52) U.S. Cl.
CPC ............. *G01N 21/59* (2013.01); *C02F 1/325* (2013.01); *G01N 33/18* (2013.01);
(Continued)

(58) Field of Classification Search
CPC ........ G01N 21/33; G01N 33/18; G01N 21/59; G01N 2201/061; C02F 1/325; C02F 2201/326; C02F 2201/3227
See application file for complete search history.

(56) References Cited

U.S. PATENT DOCUMENTS

| 6,791,092 B2 | 9/2004 | Hamilton |
| 2008/0105623 A1 | 5/2008 | Levy et al. |

(Continued)

FOREIGN PATENT DOCUMENTS

| DE | 19908583 A1 | 9/1999 |
| JP | 2005144382 A | 6/2005 |

OTHER PUBLICATIONS

International Preliminary Report on Patentability with Written Opinion for International Application No. PCT/EP2016/050765, dated Jul. 18, 2017, 5 pages.

(Continued)

*Primary Examiner* — David P Porta
*Assistant Examiner* — Faye Boosalis
(74) *Attorney, Agent, or Firm* — RatnerPrestia

(57) ABSTRACT

Method for determining the UV transmittance of water in a UV disinfection plant, through which water flows, wherein the UV disinfection plant has a plurality of radiator arrangements, each with a UV radiation source, a sleeve tube which surrounds the UV radiation source and which has an end face at an open end, and with a UV-C sensor which detects the UV radiation emerging from the sleeve tube without the influence of the water, and with at least one further UV sensor which is arranged at a distance from the sleeve tubes of the radiator arrangements, wherein the method includes the following steps: measuring the UV radiant power emerging from the sleeve tube; measuring an amount of the transmitted radiant power by the further UV sensor; and determining the transmittance of the water by an amount of (Continued)

the emerged radiant power and of the transmitted radiant power.

9 Claims, 1 Drawing Sheet

(51) Int. Cl.
*C02F 1/32* (2006.01)
*G01N 21/33* (2006.01)

(52) U.S. Cl.
CPC .............................. *C02F 2201/326* (2013.01); *C02F 2201/3227* (2013.01); *C02F 2303/04* (2013.01); *G01N 21/33* (2013.01); *G01N 2201/061* (2013.01)

(56) References Cited

U.S. PATENT DOCUMENTS

2010/0206787 A1    8/2010  Rozenberg et al.
2012/0223515 A1*   9/2012  Avramescu .......... G01N 21/359
                                                            280/830

OTHER PUBLICATIONS

International Search Report for PCT/EP2016/050765, dated Mar. 16, 2016, 10 pages.

* cited by examiner

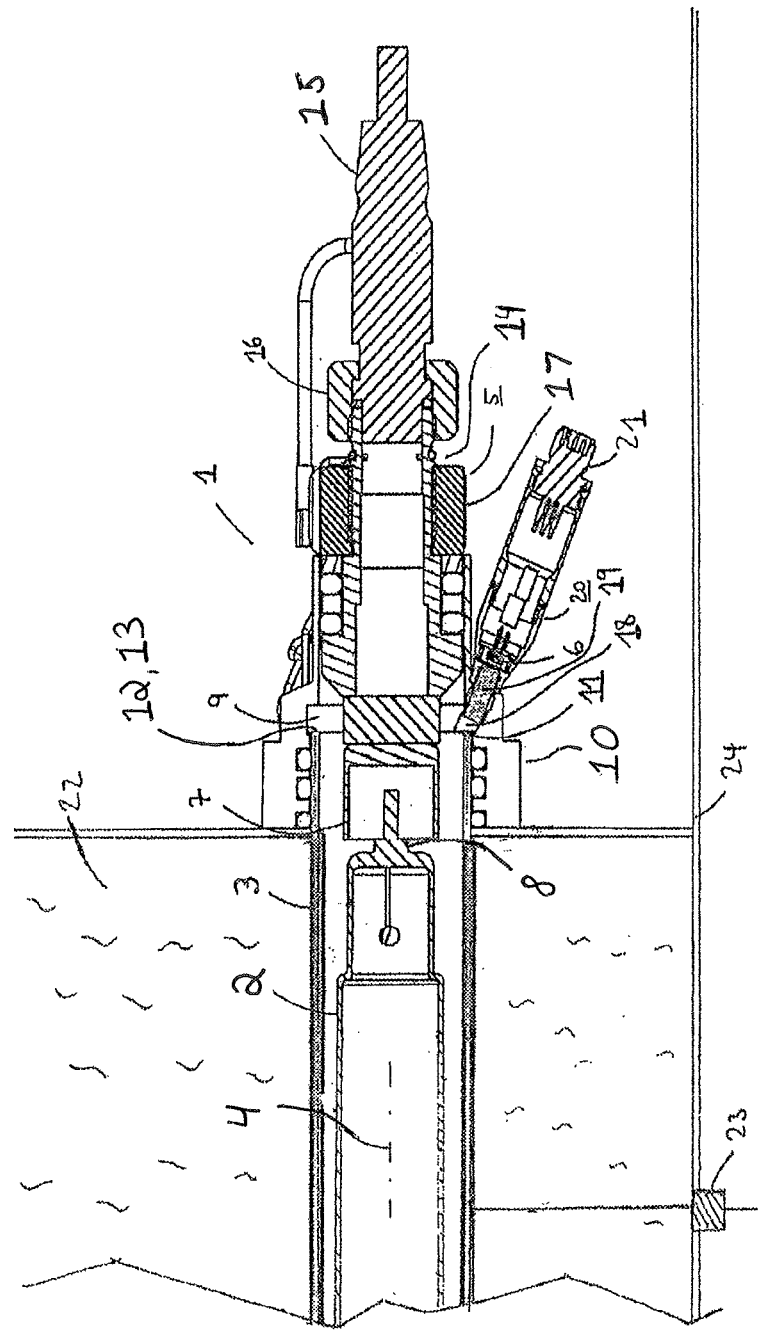

METHOD FOR DETERMINING THE UV TRANSMITTANCE OF WATER

CROSS-REFERENCE TO RELATED APPLICATIONS

This patent application is a U.S. National Phase Patent Application of PCT Application No. PCT/EP2016/050765, filed Jan. 15, 2016, which claims priority to German Patent Application No. 102015000263.5, filed Jan. 16, 2015, each of which is incorporated by reference herein in its entirety.

FIELD OF THE INVENTION

The present invention relates to a method for determining the UV transmittance of water.

BACKGROUND OF THE INVENTION

For many decades, UV radiators have been used for disinfecting drinking water and waste water in air conditioning sumps and for disinfecting working areas in biological laboratories.

In UV water treatment plants, UV-C radiation sources are arranged in a silica glass sleeve tube in order to irradiate the water. The sleeve tube protects the radiation source from external damage and simultaneously ensures an efficient operating temperature.

UV disinfection plants generally comprise a plurality of UV radiators which are arranged in a throughflow reactor, through which water flows, or in an open channel. While flowing through the reactor or the channel, the water is exposed to an adequate dose of UV-C radiation so that the desired effect is achieved. To monitor the dose released into the water, a UV sensor is conventionally provided in the reactor, which is arranged orthogonally to and at a distance from the radiator surfaces and which receives a signal which is representative of the radiant power released into the water. This measurement can also detect a change in the irradiation intensity, but it cannot detect the cause thereof. The irradiation intensity detected by a UV sensor is influenced by many factors, such as aging of the UV radiator or of the UV sensor, a coating formation on one of the silica sleeve tubes surrounding the UV radiator and a change in the quality of the water.

In this respect, the water quality is of particular interest, because the ideal dose of UV depends thereon, inter alia. The UV radiation is weakened by substances which are dissolved in the water. In particular, iron, manganese, humic acids and other organic ingredients have an influence on the UV transmittance. Therefore, the UV transmittance must be measured in order to determine the water quality. The weakening of the UV radiation by the water is heavily dependent on the wavelength. Therefore, the UV transmittance is determined using the wavelength of 254 nm which is effective for the UV disinfection of water. A separate transmission measurement method is conventionally used to measure the UV transmittance.

U.S. Pat. No. 6,791,092 B2 discloses, for example, a transmission measuring device which has an analysis chamber for the passage of a liquid, in which a UV radiator and three UV sensors, attached at different intervals from the UV radiator, are arranged. By evaluating the measurement signals, it is possible to infer the transmittance of the liquid via the shape of the arrangement.

Typical values of the UV transmittance are 85-98%/cm for drinking water and 50-75%/cm for waste water.

SUMMARY OF THE INVENTION

The object of the present invention is to provide a method for determining the UV transmittance in water which is carried out independently of the operating state and age condition of the radiation source and in which it is possible to dispense with a separate transmission measurement method.

This object is achieved by a method having the features of Claim 1.

According thereto, a method is provided for determining the UV transmittance of water in a UV disinfection plant, through which water flows, the UV disinfection plant having a plurality of radiator arrangements, each with a UV radiation source, a sleeve tube which surrounds the UV radiation source and which has an end face at an open end, and with a UV-C sensor which detects the UV radiation emerging from the sleeve tube, without the influence of the water, and with at least one further UV sensor which is arranged at a distance from the sleeve tubes of the radiator arrangements, the method having the following steps: for at least one radiator arrangement, measuring an amount of the UV radiant power emerging from the sleeve tube by means of the UV-C sensor; measuring an amount of the transmitted radiant power by means of the at least one further UV sensor arranged at a distance from the UV radiation sources; determining the transmittance of the water by means of the amount of emerged radiant power and the amount of transmitted radiant power. According to the method, the transmittance of the water can be determined although a separate transmission measurement method is not used. The UV radiation source is preferably surrounded concentrically by the sleeve tube.

The UV disinfection plant can be part of a closed throughflow reactor or it can be arranged in an open channel.

The UV-C sensor is advantageously in optical connection with the end face of the sleeve tube so that the sensitive surface of the UV-C sensor detects the UV radiation emerging from the end face of the sleeve tube. The UV radiator power emerging from the sleeve tube can thus be determined independently of external influences. In this respect, the substantially annular front of the sleeve tube is to be considered as the end face and not, for example, the entire circular cross section.

When the UV radiation emerges from the end face, this radiation passes into the material of the sleeve tube over the length of said tube and is uncoupled at the front. In contrast to methods in which the UV radiation is measured at one end inside the sleeve tube, and thus radiation is mainly detected from the end region of the radiator, measuring at the end face is more appropriate for detecting the condition and the current power of the radiator.

It is preferred that the at least one further UV sensor, arranged at a distance from the sleeve tubes, is arranged in the flowing water.

In an embodiment, in the last step of the method "determining the transmittance of the water by means of the amount of emerged radiant power and by the amount of transmitted radiant power", the transmittance of the water is determined using the shape of the UV disinfection plant.

In another embodiment, in the last step of the method, the transmittance of the water is determined by an interim value which is proportional to the transmission value and which is calculated using the logarithm of the quotient of the amount of the emerged radiant power and the amount of the transmitted radiant power.

However, instead of this, it can also be advantageous in the last step of the method to determine the water transmittance using look-up tables.

The at least one further UV-C sensor, arranged at a distance from the sleeve tubes is preferably arranged orthogonally to a circumferential surface of the sleeve tubes.

BRIEF DESCRIPTION OF THE DRAWING FIGURES

In the following, a preferred embodiment of the invention will be described in detail with reference to the drawing.

The FIGURE is a longitudinal sectional view of a radiator arrangement 1 with a radiation source 2 which is surrounded concentrically along its longitudinal axis 4 by a substantially cylindrical sleeve tube 3 consisting of UV-transparent material, and with a connection element 5 and a UV-C sensor 6.

DETAILED DESCRIPTION OF THE INVENTION

The FIGURE is a longitudinal sectional view of a radiator arrangement 1 with a radiation source 2 which is surrounded concentrically along its longitudinal axis 4 by a substantially cylindrical sleeve tube 3 consisting of UV-transparent material, and with a connection element 5 and a UV-C sensor 6. The connection element 5 has a bushing 7 which accommodates a contact base 8 of the radiation source 2. The bushing 7 passes through a circular disc 9 which, in cooperation with a sealing system 10 surrounding the sleeve tube 3 in the region of the bushing 7, acts as a seat 11 for the sleeve tube 3 at its open end 12. The sleeve tube 3 has a uniform wall thickness and is cut off at its end 12 vertically to its longitudinal axis 4, thereby forming an annular end face 13. The end face 13 is in at least partial contact with the disc 9. The sealing system 10 outwardly seals the sleeve tube 3. The bushing 7 of the connection element 5 is connected to an electrical connection 14 for a connecting plug 15 of the radiator arrangement 1. The connecting plug 15 is attached by a cap nut 16 to the connection 14, which is part of the connection element 5. A second cap nut 17 is provided to assemble the sealing system 10.

In the region of the seat 11 for the sleeve tube 3, the disc 9 has a penetrating recess 18 in which a coupling optics 19 of the UV-C sensor 6 is at least partly arranged. The UV-C sensor 6 is connected to an electrical connecting plug 21 by a connection element 20.

The light generated by the UV radiation source 2 is diffracted on passing through the UV-transparent material of the sleeve tube 3. The sleeve tube 3 preferably consists of silica glass. In this respect, there is total reflection to some extent. Thus, some of the light remains in the sleeve tube 3 and is reflected back and forth there. The sleeve tube 3 thereby acts as a type of semiconductor. The UV radiation emerges at the end face 13 of the sleeve tube 3 and is delivered to the sensor 6 by the coupling optics 19 via an air gap. It can also be provided that the coupling optics 19 is coupled directly to the end face 13. Furthermore, a direct axial coupling of the sensor 6 to the end face 13 with or without an air gap can also be appropriate. It is advantageous in all cases if the UV sensor 6 has an edge filter. In the embodiment shown here, only some of the light emerging from the annular end face 13 is used for the measurement.

In another embodiment, it is provided that suitable optical transition pieces are used which allow a more comprehensive use or even full use of the radiation emitted from the annular end face 13.

The coupling surface of the sensor 6 or of the coupling optics 19 does not necessarily have to extend orthogonally to the longitudinal axis of the radiation source 4.

The UV-C sensor 6 preferably has a silicon carbide (SiC) diode.

The UV radiator arrangement is part of a throughflow reactor of a UV radiation plant. The connection elements and the electrical connections of the UV radiator arrangement project out of the water 22. Provided in addition to the UV-C sensor 6 associated with the UV radiator arrangement is a further UV sensor 23 which is arranged at a distance from the sleeve tube 3, for example as shown here, in the region of the wall 24 bordering the reactor. This UV sensor 23 which is arranged at a distance is conventionally provided to measure the irradiation intensity in the water. In this respect, it is oriented with its measurement axis preferably orthogonally to the surface of the sleeve tube 3.

The water transmittance T of a layer thickness d can be determined using the Beer-Lambert law by determining the entering and transmitted radiant power. The UV radiator arrangement 1 measures the irradiation intensity independently of the water transmittance T. Thus, the absolute radiant power entering the water can be specified while bearing in mind the construction of the reactor. The sensor 23 arranged at a distance from the sleeve tube 3 receives a signal which is representative of the transmitted radiant power. If the radiation source 2 is subjected to fluctuations during operation, this has an effect, as it were, on the two measured variables of the two sensors 6, 23 which provide a measurement for the emerged radiant power and a measurement for the transmitted radiant power. The logarithm of the quotient of the radiation values from the two UV-C sensors 6, 23 then provides a result which is proportional to the transmission value and which can be standardised via the shape of the plant.

However, it can also be provided to standardise the measurement of the water transmittance by a measurement with, for example, ultrapure water. Using a look-up table, it is then possible to infer the water transmittance from the measured amount for the emerged radiant power and from the amount for the transmitted radiant power.

After the initial installation of a UV disinfection plant with a plurality of UV radiator arrangements according to the invention, a standardisation measurement is made in which the signal, measured by the UV sensors, is recorded. This standardisation measurement makes it possible to determine the relative irradiation intensity of the individual radiators during operation of the plant, independently of the previously mentioned embodiments. Thus, during the operation of a multiple radiator plant, it is possible to measure the water transmittance and to directly compare radiation proportions of all installed radiation sources.

The present invention provides a method for determining the UV transmittance in water which is carried out independently of the operating state and aging condition of the radiation source, and in which it is possible to dispense with a separate transmission measurement method. The method can be used for single and multiple radiator plants.

The decoupled radiation proportion of the radiator arrangement is representative of the radiator power and is an indication of the radiation flow of the UV radiation into the water. Although, here as well, adjacent radiation sources also contribute a signal component to the measurement signal of the UV-C sensor 6 associated with the individual radiator, this component is virtually insignificant.

The UV-C sensor 23 arranged at a distance from the sleeve tube measures the transmitted radiant power, so that by evaluation of the sensors, it is possible to infer the water transmittance or the water quality in a reliable and cost-effective manner.

The invention claimed is:

1. A method for determining an ultraviolet (UV) transmittance of water in a UV disinfection plant, through which water flows, wherein the UV disinfection plant includes:
   a plurality of radiator arrangements, each arrangement comprising a UV radiation source, a sleeve tube surrounding the UV radiation source and having an annular end face at an open end, and a UV-C sensor that is in optical connection with the annular end face of the sleeve tube so that a sensitive surface of the UV-C sensor detects UV radiation emerging from the sleeve tube without the influence of the water, and
   at least one further UV sensor arranged at a distance from (i) the sleeve tubes of the radiator arrangements and (ii) the UV radiation sources,
   wherein the method comprises:
   a) for at least one radiator arrangement, measuring with the sensitive surface of the UV-C sensor an amount of UV radiant power emerging from the annular end face of the sleeve tube that is in optical connection with the UV-C sensor without the influence of water passing between the UV-C sensor and the annular end face of the sleeve tube;
   b) measuring with the at least one further UV sensor an amount of transmitted radiant power;
   c) determining the transmittance of the water based upon the amount of transmitted radiant power relative to the amount of emerged radiant power.

2. The method according to claim 1, wherein the at least one further UV sensor is arranged in the flowing water.

3. The method according to claim 1, wherein in step c), the water transmittance is determined using a shape of the UV disinfection plant.

4. The method according to claim 1, wherein in step c), the water transmittance is determined by an interim value which is proportional to a transmission value and is calculated by a logarithm of a quotient of an amount of the emerged radiant power and of an amount of the transmitted radiant power.

5. The method according to claim 1, wherein in step c), the water transmittance is determined using look-up tables.

6. The method according to claim 1, wherein the at least one further UV-C sensor is arranged orthogonally to a circumferential surface of the sleeve tubes.

7. A UV disinfection plant through which water flows, the UV disinfection plant comprising:
   (a) a plurality of radiator arrangements, each arrangement comprising:
      (i) a UV radiation source,
      (ii) a sleeve tube surrounding the UV radiation source and having an annular end face at an open end, and
      (iii) a UV-C sensor configured to detect UV radiation emerging from the sleeve tube without the influence of the water, wherein an air gap separates the UV sensor from the sleeve tube and the UV radiation source, and
   (b) at least one further UV sensor arranged at a distance from (i) the sleeve tubes of the radiator arrangements and (ii) the UV radiation sources
   wherein, for each radiator arrangement, the UV-C sensor is in optical connection with the annular end face of the sleeve tube, so that a sensitive surface of the UV-C sensor detects the UV radiation emerging from the annular end face of the sleeve tube without the influence of water passing between the UV-C sensor and the annular end face of the sleeve tube.

8. The UV disinfection plant according to claim 7, wherein the at least one further UV sensor is arranged in the flowing water.

9. The UV disinfection plant according to claim 7, wherein the at least one further UV-C sensor is arranged orthogonally to a circumferential surface of the sleeve tubes.

* * * * *